(12) United States Patent
Hobbs et al.

(10) Patent No.: US 9,440,046 B2
(45) Date of Patent: Sep. 13, 2016

(54) VENOUS INSUFFICIENCY TREATMENT METHOD

(75) Inventors: Eamonn Hobbs, Queensbury, NY (US); William M. Appling, Granville, NY (US)

(73) Assignee: Angiodynamics, Inc., Latham, NY (US)

( * ) Notice: Subject to any disclaimer, the term of this patent is extended or adjusted under 35 U.S.C. 154(b) by 2481 days.

(21) Appl. No.: 11/303,818

(22) Filed: Dec. 15, 2005

(65) Prior Publication Data

US 2006/0095015 A1  May 4, 2006

Related U.S. Application Data

(63) Continuation-in-part of application No. 10/393,922, filed on Mar. 20, 2003, now Pat. No. 7,163,533.

(60) Provisional application No. 60/370,050, filed on Apr. 4, 2002.

(51) Int. Cl.
*A61M 25/00* (2006.01)
*A61B 18/24* (2006.01)
*A61B 17/00* (2006.01)
*A61B 17/22* (2006.01)

(52) U.S. Cl.
CPC ........ *A61M 25/0075* (2013.01); *A61B 18/245* (2013.01); *A61B 17/00008* (2013.01); *A61B 2017/00778* (2013.01); *A61B 2017/22082* (2013.01); *A61M 25/007* (2013.01); *A61M 2025/0076* (2013.01)

(58) Field of Classification Search
CPC .................... A61M 25/0054; A61M 25/0147
USPC .................. 128/898; 604/523, 528, 264
See application file for complete search history.

(56) References Cited

U.S. PATENT DOCUMENTS

| | | | | | |
|---|---|---|---|---|---|
| 4,666,426 | A | * | 5/1987 | Aigner | 604/6.16 |
| 4,968,306 | A | * | 11/1990 | Huss et al. | 604/264 |
| 5,250,034 | A | | 10/1993 | Appling et al. | |
| 5,267,979 | A | * | 12/1993 | Appling et al. | 604/247 |
| 5,330,467 | A | | 7/1994 | Abela | |
| 5,425,723 | A | * | 6/1995 | Wang | 604/523 |
| 5,575,787 | A | | 11/1996 | Abela et al. | |
| 5,782,797 | A | * | 7/1998 | Schweich et al. | 604/507 |
| 5,999,678 | A | | 12/1999 | Murphy-Chutorian et al. | |
| 6,117,125 | A | * | 9/2000 | Rothbarth et al. | 604/523 |
| 2001/0016739 | A1 | * | 8/2001 | Goldman et al. | 606/32 |
| 2002/0007181 | A1 | | 1/2002 | Jones et al. | |
| 2003/0120256 | A1 | * | 6/2003 | Lary et al. | 604/509 |
| 2005/0107738 | A1 | * | 5/2005 | Slater et al. | 604/96.01 |
| 2005/0113798 | A1 | * | 5/2005 | Slater et al. | 604/508 |

* cited by examiner

*Primary Examiner* — William Thomson
*Assistant Examiner* — Jeffrey Lipitz
(74) *Attorney, Agent, or Firm* — Peter Flora (57) ABSTRACT

The method of treating varicose veins and other vascular diseases provides sclerosant fluid through a catheter into the body vessel to be treated. The catheter has a lumen and a plurality of sidewall exits. The sclerosant fluid is provided under sufficient pressure so that it comes out of each exit as a jet of fluid with sufficient velocity to impinge on the vessel wall substantially orthogonal to the wall and thus minimize dilution of the sclerosant fluid and optimize coverage. A movable sheath on the catheter permits selecting a portion of the exits to be uncovered and thus create an infusion zone for the jets of sclerosant fluid which approximately match a desired treatment zone.

33 Claims, 4 Drawing Sheets

VENOUS INSUFFICIENCY TREATMENT METHOD

CROSS-REFERENCE TO RELATED APPLICATIONS

This application is a continuation-in-part of U.S. patent application Ser. No. 10/393,922, filed Mar. 20, 2003 now U.S. Pat. No. 7,163,533, which claims priority to U.S. Provisional Application No. 60/370,050, filed Apr. 4, 2002, all of which are incorporated herein by reference.

FIELD OF THE INVENTION

The present invention relates to a method for treatment of vascular diseases, and more particularly, to a method for treating varicose veins using catheter and sclerosing agent.

BACKGROUND OF THE INVENTION

Veins are thin-walled and contain one-way valves that control blood flow. Normally, the valves open to allow blood to flow into the deeper veins and close to prevent back-flow into the superficial veins. When the valves are malfunctioning or only partially functioning, however, they no longer prevent the back-flow of blood into the superficial veins. As a result, venous pressure builds at the site of the faulty valves. Because the veins are thin walled and not able to withstand the increased pressure, they become what are known as varicose veins which are veins that are dilated, tortuous or engorged.

In particular, varicose veins of the lower extremities are one of the most common medical conditions of the adult population. It is estimated that varicose veins affect approximately 25% of adult females and 10% of males. Symptoms include discomfort, aching of the legs, itching, cosmetic deformities, and swelling. If left untreated, varicose veins may cause medical complications such as bleeding, phlebitis, ulcerations, thrombi and lipodermatosclerosis.

Traditional treatments for varicosities include both temporary and permanent techniques. Temporary treatments involve use of compression stockings and elevation of the diseased extremities. While providing temporary relief of symptoms, these techniques do not correct the underlying cause that is the faulty valves. Permanent treatments include surgical excision of the diseased segments, ambulatory phlebectomy, and occlusion of the vein through thermal means.

Surgical excision requires general anesthesia and a long recovery period. Even with its high clinical success rate, surgical excision is rapidly becoming an outmoded technique due to the high costs of treatment and complication risks from surgery. Ambulatory phlebectomy involves avulsion of the varicose vein segment using multiple stab incisions through the skin. The procedure is done on an outpatient basis, but is still relatively expensive due to the length of time required to perform the procedure.

Minimally invasive thermal treatments for venous insufficiency eliminate the need for general anesthesia and have relatively short recovery times. Endovascular thermal energy therapy is a relatively new treatment technique for venous reflux diseases. With this technique, thermal energy in the form of laser or radio frequency (RF) energy is delivered by an energy delivery device that is percutaneously inserted into the diseased vein prior to energy delivery. In a laser therapy, an optical fiber is used as the energy delivery device whereas in an RF therapy, RF electrodes are used as the energy delivery device. The procedure for the thermal energy therapy involves inserting an introducer catheter or sheath and advancing it to within a few centimeters of the sapheno-femoral junction of the greater saphenous vein. In the case of laser therapy, once the introducer catheter is properly positioned, a flexible optical fiber is inserted into the lumen of the catheter or sheath and advanced until the distal fiber tip is near the catheter tip but still protected within the catheter lumen.

Once the energy delivery device is positioned within the vein, the tissue immediately surrounding the diseased vessel segment is subjected to numerous needle punctures to make percutaneous injections of a tumescent anesthetic agent. The injections, typically Lidocaine with or without epinephrine, are administered under ultrasonic guidance along the entire length of the greater saphenous vein into the perivenous space. The tumescent injections perform several functions. First, the anesthetic injection inhibits pain caused from the application of energy to the vein. Second, the injection reduces the diameter of the vein to facilitate efficient energy transmission to the vessel wall. Third, the tumescent injection also provides a barrier between the vessel and the adjacent tissue and nerve structures, which restricts the heat damage to only the vessel itself and prevents non-target tissue damage. After the anesthetic injections are made through multiple puncture sites, the energy delivery device is withdrawn as thermal energy is transferred to the inner vein wall causing cell necrosis and eventual vein collapse.

For thermal treatment, the injection of tumescent anesthesia through multiple punctures along the diseased segment is considered a standard and necessary step in the treatment protocol. However, there are several disadvantages associated with such a conventional method of administering local anesthesia injections. The anesthetic injection process is cumbersome and is the most time-consuming step in the treatment procedure because of the number of punctures that has to be made. Typically, injections are administered along the entire length of the greater saphenous vein in 2-3 cm increments. The total injection length varies but is usually between 30 and 40 cm.

Although these minimally invasive thermal treatments have been shown to be effective and safe in eliminating the cause of varicosities, they have procedural shortcomings and complications that make them less than ideal. As discussed above, administration of tumescent anesthesia along the vein segment being treated requires careful administration and significant preparation time. In addition, reported thermal treatment complications include pain for up to ten days following treatment, extensive bruising caused by vessel perforations, paresthesias, deep vein thrombosis and skin burns. The energy generator and disposable devices necessary to perform the procedure are expensive and require capital investment by the practitioner. Another drawback of thermal treatment of venous disease is the delivery device, which limits treatment to veins of a diameter that will accommodate the device. Very tortuous veins cannot be treated by thermal ablation because the catheter cannot successfully navigate the vein path.

Chemical occlusion, also known as sclerotherapy, is an in-office procedure involving the injection of an irritant chemical directly into the vein. The drug is delivered either through direct injections with a small gauge needle or more recently using a catheter placed in the target vein. The chemical acts upon the inner lining of the vein walls causing them to occlude and block blood flow. The use of liquid sclerosing agents to treat varicosities has been utilized for decades, but has traditionally been limited to veins with diameters less than 5 mm.

Sclerotherapy to treat larger diameter veins has not been widely used due mainly to recommended volume limit of the drug and reported failure rates. Sufficient drug must be delivered to the treatment zone to fully displace the blood. A typical sclerosant, such as 3% sodium tetradecyl sulfate, is volume limited to a maximum of 10 cc per treatment, making it difficult to treat larger veins. Catheter-directed sclerotherapy has been attempted in larger veins such as the Great Saphenous Vein using liquid sclerosant. Although initially successful, long-term failure rates are reportedly high, due to inadequate concentrations of drug being delivered to the vessel to cause durable closure and permanent destruction of the vein. It is also postulated that blood flow in larger veins prevents the sclerosant from reaching the vessel wall in sufficient concentration to effectively destroy the inner vessel wall lining to occlude the vessel, resulting in a relatively low treatment success rate.

To minimize the dilution of the agent by blood, some practitioners have utilized methods of emptying as much blood volume as possible from the vein being treated. Vein emptying may be performed by placing the patient in a Trendelenberg position with the target leg higher than the torso. Emptying may also be facilitated by the use of manual compression using either compression bandages or finger compression at the proximal and distal ends of the vein. These techniques, while lowering the overall blood volume in the vessel, are time-consuming, require additional personnel to maintain compression during the procedure, are uncomfortable to the patient, and often result in incomplete blood removal and inconsistent treatment results.

Another sclerotherapy treatment that has recently emerged involves the use of a foamed sclerosant to treat larger veins. A liquid sclerosing agent can be converted to a foam agent by forcing gas into the liquid, whereby creating microbubbles. Foam has several advantages over liquid sclerosant. Foamed sclerosing agents provide an increased concentration of the sclerosing agent against the vessel wall. The theory is that the foam displaces the blood in the vessel as the sclerosant is carried on the exterior of the bubble. The foam contacts the vein wall delivering high concentrations of the drug to the vein wall while minimizing the amount of drug introduced in to the patient. Theoretically, these microbubbles contact and adhere more effectively to the vessel wall than liquid because of their increased surface tension. Increased concentration of sclerosant allows the practitioner to use lesser amounts than with liquid sclerosant, whereby decreasing potential complications associated with larger drug volumes. A further advantage of foam is that as it is injected, the foam displaces the blood locally, whereby minimizing the possibility of ineffective closure due to dilution of the sclerosant by the blood. The displacement of blood allows the practitioner to use less sclerosant.

When treating a vein with foam, some form of image guidance must be used to insure foam reaches the intended location and does not enter the deep venous system through the connecting perforating and tributary veins. The gas bubbles in the foam make it visible under ultrasound or a contrast agent may be mixed with the foam for visualization using fluoroscopy.

While foam has been demonstrated to be more effective in vein closure compared with infused liquid, it may cause significant neurological and systemic complications if it travels to the arterial system. The gas bubbles that escape the superficial vessel and migrate to the deep venous system are normally filtered out by the lung, but if the patient has a patent foramen ovale (septal defect in the heart present in approximately one-fourth the population), bubbles may pass from the venous system into the arterial system, resulting in temporary visual problems, reduced cognitive functioning and other more serious side effects such as stroke. The procedure must be closely monitored to prevent the expanding foam from entry into the deep venous system through tributaries or perforating veins.

Some sclerotherapy delivery devices utilize one or more occlusion elements to isolate the treatment area, whereby minimizing dilution of the drug and reducing the total volume necessary for treatment. Once the device is properly positioned, the balloons or other occlusion elements are inflated, creating an isolated vein segment to which the sclerosant is delivered. The balloons temporarily occlude blood flow through the isolated segment and also prevent the migration of drug into the deep venous system. These devices, while effective in isolating the treatment area, are complicated devices which are expensive to manufacture and require additional training to use. In addition, complications can occur when the sclerosant is injected into the isolated segment. The pressure within the isolated segment, by the injection of sclerosant, may force the sclerosant into the deep venous system through perforator veins. This situation can lead to deep vein thrombosis, and in the case of foam sclerosant, may cause microbubbles to travel to the pulmonary system.

Therefore, it is desirable to provide an effective method of treating venous reflux utilizing a fluid sclerosant agent that targets the vessel wall without dilution. The method should avoid the associated complications of foam migration to the deep venous system. The method should not require emptying the vessel of blood. The method should be able to treat large diameter veins without having to isolate vein segments using complicated occlusion devices. It is cumbersome and time-consuming to monitor the sclerosant as it is delivered to ensure injected volumes are insufficient to migrate through the perforators into the deep venous system. A method which eliminates or minimizes monitoring and instead uses controlled volumes is desirable. Further, it is desirable to provide a method of vein closure that does not require complicated and expensive equipment and delivery devices, and is simple and fast for the practitioner. It would be advantageous for the method to be performed using a catheter based system to avoid the time and complications associated with direct stick injections. Optimally, the use of time-consuming tumescent anesthesia would be eliminated with this method. Finally, it would be advantageous to provide a method of treatment that minimizes the total volume sclerosant required for the procedure by directing concentrated drug directly at the vessel wall.

BRIEF DESCRIPTION

In brief, the presently preferred embodiment of the method of treating a vascular disease includes insertion of a catheter into a patient's body vessel. The catheter has a lumen for receiving sclerosant fluid and a plurality of exits through which the sclerosant fluid is emitted under pressure as jets of fluid into the body lumen. The jets of fluid impinge on the wall of the body vessel and cover a treatment zone of the body vessel.

A moveable sheath over the catheter permits the uncovering of a predetermined portion of the exits, which portions can be up to 100 percent, so as to permit the selection and targeting of a treatment zone.

The jets of fluid preferably have sufficient force so as to impinge on the wall of the vessel substantially orthogonal to the wall of the vessel to spread out over the vessel wall and to be minimally diluted by the ambient blood.

BRIEF DESCRIPTION OF THE DRAWINGS

FIG. 2A illustrates the use of an occluding ball wire to close the distal end hole of the catheter.

FIG. 2B illustrates the use of a standard guidewire to close the end hole.

FIG. 3A-3E is a series of plan views of the device within the vein depicting the method of the current invention.

DESCRIPTION OF THE PREFERRED EMBODIMENTS

Figure 1:
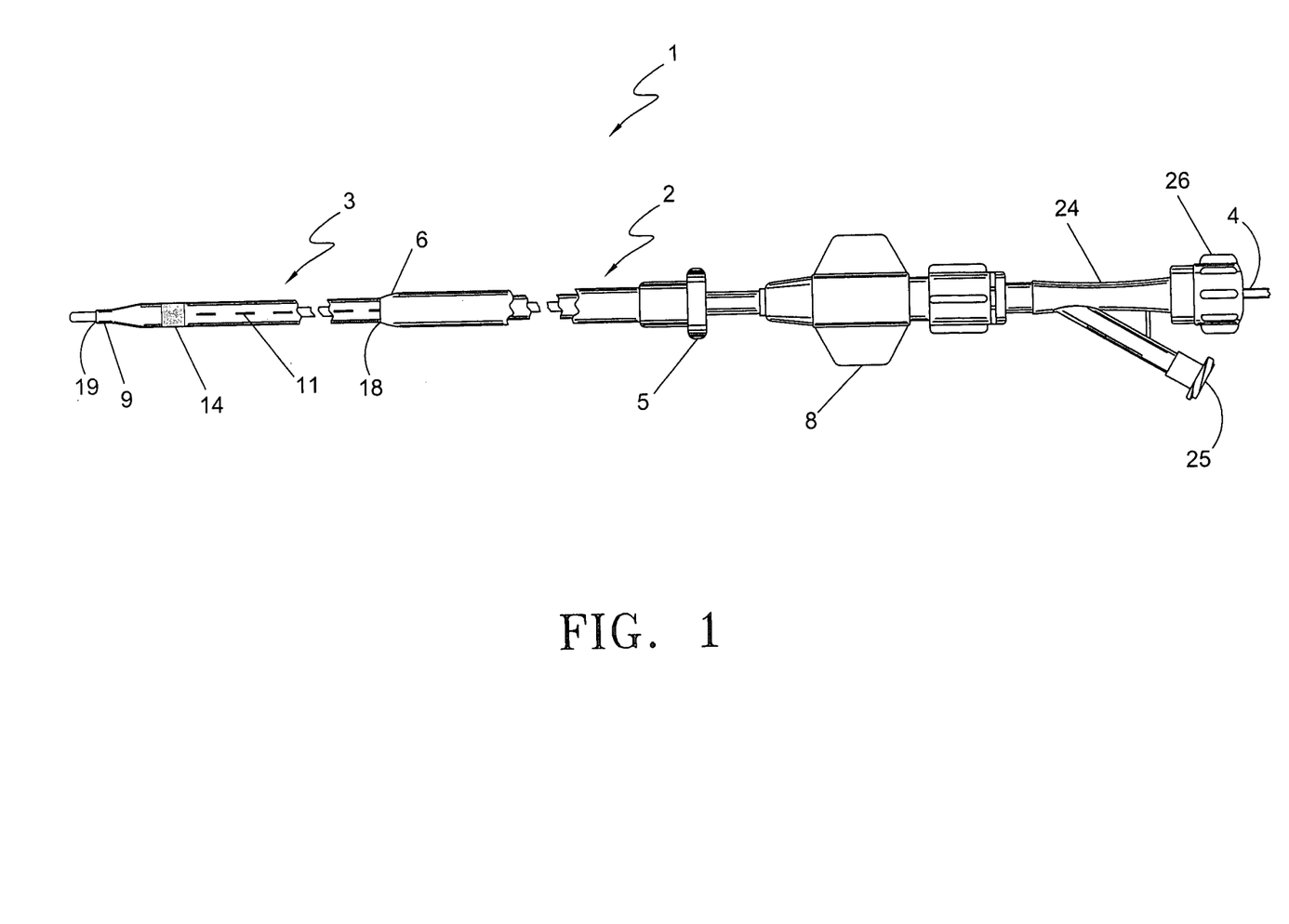
FIG. 1 illustrates a catheter/sheath assembly device with an occluding wire for use in the method according to the present invention.

A method of treating venous reflux utilizing a sclerosant agent will now be described. The method of sclerosing a vessel utilizes a catheter/sheath assembly device 1, illustrated in FIG. 1 and in FIGS. 2A and 2B. FIG. 1 is a plan view of the assembled device shown with an occluding ball wire 4. The sheath 2 is comprised of a sheath hub 5, a distal tip section 6, a lumen extending from the sheath hub 5 to the distal tip 6 and terminating in a sheath end hole 18. The sheath hub 5 may include a seal to prevent blood and sclerosant from leaking. The sheath 2 body may be reinforced with ultrasonically visible material such as braided or helically wound medical grade stainless steel wire. The reinforced shaft provides the user with enhanced flexibility and pushability in addition to improved visibility under ultrasound.

The catheter component 3 is coaxially arranged within the sheath lumen and is comprised of a catheter hub 8, a distal tip 9, and a lumen 10 extending from catheter hub 8 to the distal tip 9 and terminating in catheter end hole 19. Extending along a portion of the catheter are normally closed pressure responsive exits or outlets 11 which form an infusion zone 20, shown in FIGS. 2A and 2B. The maximum length of the infusion zone 20 is identified by radiopaque markers 14 located at the distal and proximal end of the infusion zone. As shown in FIG. 1, connected to the catheter hub 8 is a standard Y-hub connector 24 to provide a port for injecting the fluid sclerosant. A compression gasket 26, such as a touhy-borst gasket is tightened around the guidewire to prevent drug leakage proximally.

The distal tip of the catheter 3 and sheath 2 may be designed to enhance visibility under fluoroscopy and/or ultrasound. The distal tip portion of catheter or sheath may be loaded with tungsten or other radiopaque filler to increase the density whereby providing enhanced radiographic visibility. Additionally, the distal tip of either component may be designed for enhanced visibility under ultrasound by incorporating structure to increase echogenicity. The tip of the sheath is visible under fluoroscopy and ultrasound so that, in conjunction with the distal marking on the catheter, the length of the infusion zone can be adjusted to match the treatment zone. Examples of such structures that will increase ultrasonic reflection include incorporating microspheres containing a gas into the tip, a band of braiding or other metallic material embedded within the tip and a tip containing an enclosed air space. As will be discussed in more detail below, the occluding ball of the occluding wire embodiment may also be designed for enhanced visibility. Other methods of incorporating imaging visibility elements within the catheter and/or sheath are known within the art and are incorporated herein.

Figure 2A:
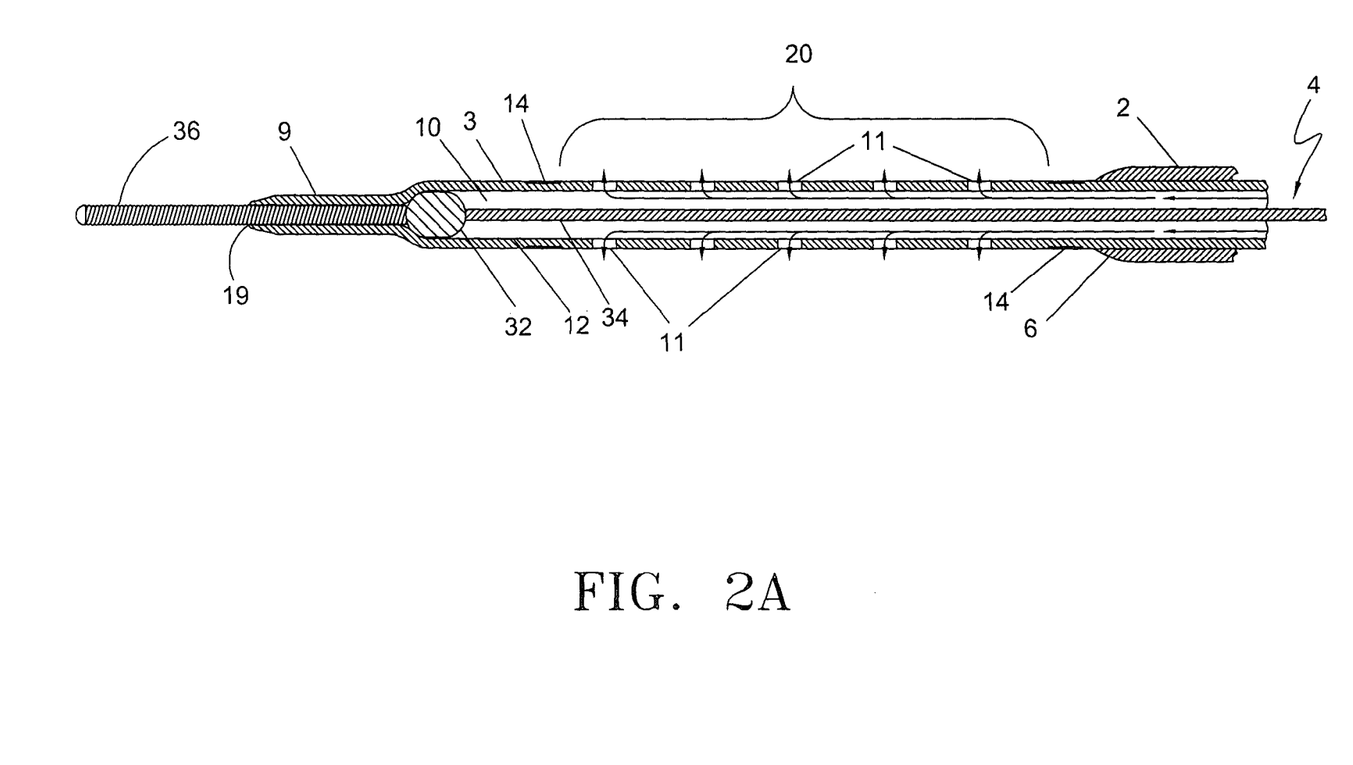
FIGS. 2A and 2B are each an enlarged sectional view of the distal end of the device illustrating fluid flow path.

FIG. 2A illustrates a method in accordance with the device and technique described in U.S. Pat. No. 5,250,034 and U.S. Pat. No. 6,283,950. An occluding ball wire 4 is comprised of a wire 34, a distal hole occluding ball 32, and a floppy distal end segment 36 which extends distally beyond the catheter end hole 19. The occluding ball 32 seats within the internal distal taper of the catheter, sealing and preventing fluid flow through the end hole. The occluding ball 32 may be formed of echogenically visible material to enhance visibility of the catheter distal tip under ultrasound guidance.

The Y-connector hub 24 shown in FIG. 1 is connected to catheter hub 8 and is used to facilitate the delivery of sclerosant through the side arm 25. Alternatively, the Y-connector hub 24 may not be necessary if the occluding wire terminates within the body of the hub, as described in U.S. Pat. No. 6,283,950. The hub may include a through lumen for the introduction of sclerosant fluid into the catheter lumen. In this occluding ball embodiment, the physician injects the sclerosant directly through occluding wire hub.

Figure 2B:
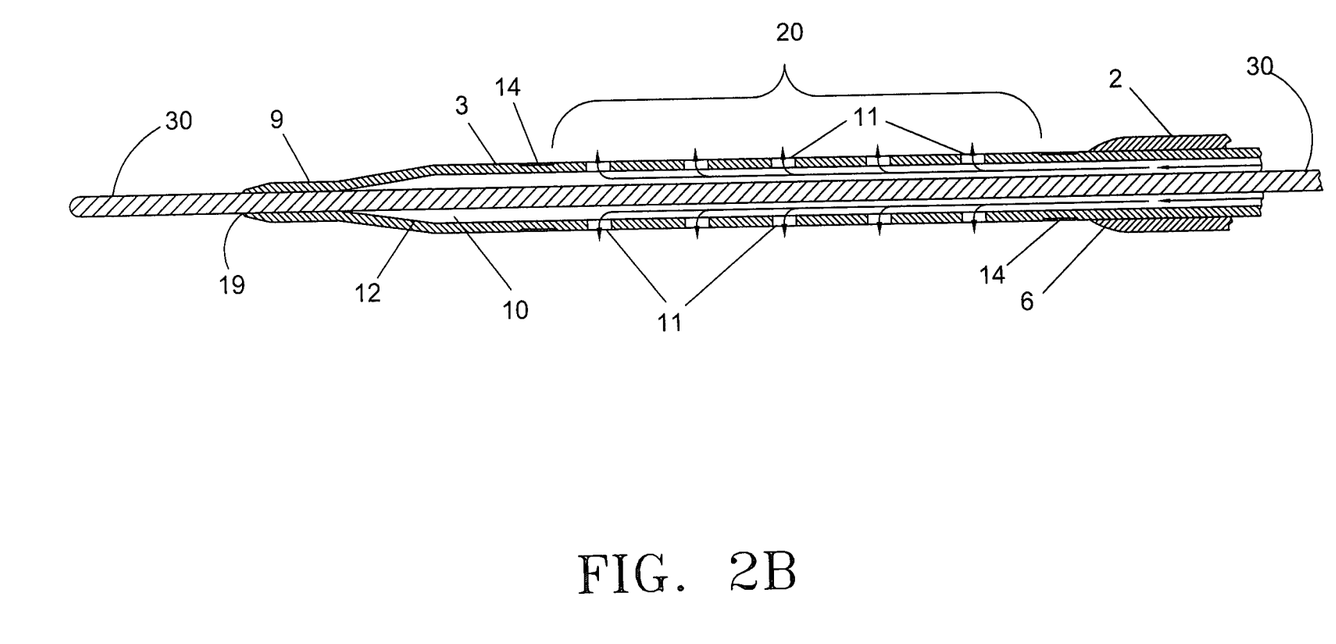

FIG. 2B illustrates use of a standard guidewire 30 for occlusion of the catheter end hole 19. As shown in FIG. 2B, the catheter end hole 19 is dimensioned to fit snuggly against the outer diameter of the guidewire 30, effectively occluding end hole 19 and creating an annular fluid channel 10 between the guidewire 30 and inner wall 12 of the catheter. As an example, a 5 French catheter has a 0.067 inch outer diameter and a 0.048 inch inner diameter. The catheter lumen tapers down distally to an end hole 19 having an inner diameter of approximately 0.036 inch to ensure occlusion by standard 0.035 inch guidewire. A 5 French sheath would have dimensions of 0.085 inch outer and 0.068 inch inner diameters. The sheath tip 6 would be sized to seal upon the catheter outer wall. Other dimensions are within the scope of this invention.

The length of the catheter is dependent on the vein being treated. If the origin of reflux is associated with the Great Saphenous Vein for example, the vein segment being treated would typically range from 30-40 cm. A vein segment of this length would need a catheter with an infusion zone 20 of approximately 40 cm to ensure complete drug coverage of the vein wall. During operation, the sheath 2 is retracted relative to the catheter 3 to uncover the desired length of the infusion zone 20. A catheter measuring approximately 80 cm in length would allow the sheath to be retracted the 40 cm needed to fully expose the entire infusion zone. Shorter catheters with shorter length infusion zones could be used to treat smaller length segments.

The infusion zone 20 is comprised of a pattern of pressure responsive outlets 11 which, by example, are each approximately 0.015 to 0.30 inch in length. A typical outlet pattern includes sets of four outlets located every 90° radially along the distal shaft of the catheter 3. The outlets 11 are approximately 5 mm apart in rows that are parallel to each other. Other outlet 11 dimensions and infusion zone patterns are within the scope of this invention.

As will be described in greater detail later, a syringe containing the sclerosant fluid is used to inject the fluid through the port 25 of the Y-hub connector 24. The fluid flows through annular channel 10 exiting through those pressure responsive outlets 11 that are not covered by the sheath.

The sheath also functions to protect the insertion site track from the unintentional delivery of sclerosant into the adjacent tissue. Injection of sclerosant into tissue is known to cause tissue necrosis, which may lead to skin ulceration and other complications. If the user misaligns the catheter so that one or more outlets are within the insertion track yet outside of the vein, subsequent injection of sclerosant will flow through the outlets and penetrate the tissue immediately surrounding the insertion track. Because the distal end of the sheath is readily visible, placing the catheter through a sheath prevents this potential complication by ensuring that all outlets outside of the vein are covered by the sheath wall thus preventing sclerosant from being delivered externally to the vein. An introducer sheath can be employed to perform this protective function.

The method of using device 1 will now be described with reference to FIG. 3A-3E. The treatment procedure begins with the standard pre-operative preparation of the patient as is well known in the treatment art. The patient is examined with ultrasound to identify and locate the source of venous reflux, typically the Great Saphenous Vein. Treatment is not necessarily limited to the Great Saphenous Vein; diseased segments of the small saphenous vein and other veins may be treated using the improved method described herein. The sapheno-femoral junction and any anatomical variations of the venous system are also identified during pre-treatment ultrasound. After the ultrasound examination, the patient's leg is draped and cleansed in preparation for the procedure.

With prior art thermal treatment methods, the patient's diseased venous segments are marked on the skin surface. Typically, ultrasound guidance is used to map the greater saphenous vein from the sapheno-femoral junction to the popliteal area. The physician marks the route of the vein with a marker under ultrasound guidance. The purpose of this mapping is to provide a visual identifying line for the physician to follow when injecting perivenous tumescent anesthesia along the length of the diseased vein. As persons of ordinary skill in the art can appreciate, mapping of the vein is a very time-consuming step for the physician. The present invention advantageously minimizes the time spent mapping the vein since tumescent anesthesia is not required with the method of the current invention.

Administration of tumescent anesthesia typically involves making 10 to 20 needle punctures to deliver 10 to 20 perivenous injections under ultrasound guidance. The injections are time-consuming, can be painful to the patient, leave multiple puncture wounds and may increase bruising and post-procedure complications. According to the principles of the present invention, however, the delivery of tumescent anesthesia is eliminated. Instead, only a small injection of local anesthesia is necessary at the entry site.

Figure 3A:
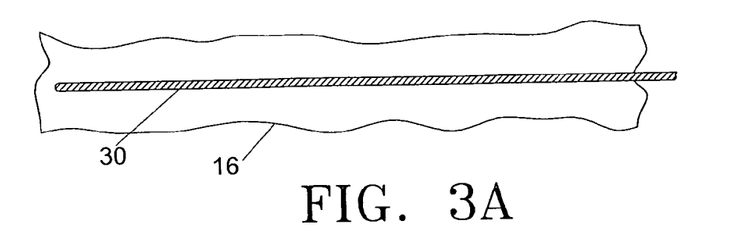
FIG. 3A depicts a plan view of a vein segment to be treated with the guidewire in place.

After the patient has been prepped, the Great Saphenous Vein is accessed using a standard Seldinger technique. A small gauge needle is inserted through the skin and into the vein lumen. A guide wire 30 is inserted through the needle and advanced to the sapheno-femoral junction. The entry needle is removed, leaving the guidewire 30 in place within the vein 16, as shown in FIG. 3A. The sheath/catheter assembly 1 is then advanced over the guidewire 30 into the vein and tracked over the wire until the assembly distal end is located just proximal of the sapheno-femoral junction. Advancement of the device 1 through tortuous vein segments is facilitated by the flexible material of the device which tracks through the curvature of the vessel lumen without kinking. Navigating through tortuous vessel segment is more difficult with prior art thermal treatment devices such as an RF electrode catheter or laser fiber, which are stiff and do not track as easily.

Figure 3B:
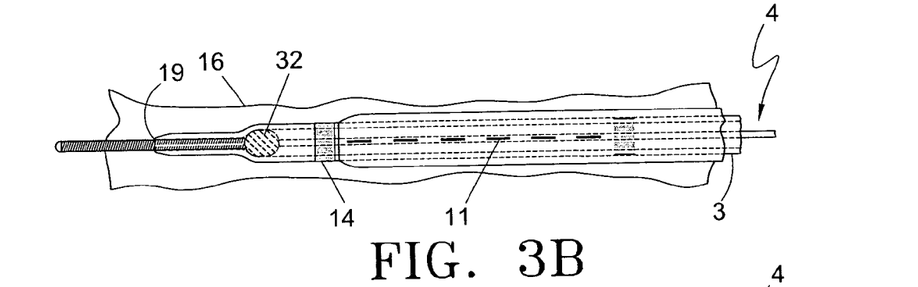
FIG. 3B is a plan view of the vein segment to be treated with the catheter/sheath assembly device with occluding ball wire within the vein.

Once the catheter/sheath assembly is properly positioned within the target vein 16, the guidewire 30 is removed. The occluding ball wire 4 is then inserted through the catheter and advanced until the occluding ball 32 seats against the inner taper of the catheter distal tip, effectively sealing the distal end hole 19, as shown in FIG. 3B. If a standard guidewire is being used rather than an occluding ball wire, the guidewire 30 remains in place within the lumen 10 of the catheter 3 during the procedure, such that the guidewire effectively occludes the end hole 19, as previously illustrated in FIG. 2B.

The placement of the catheter/sheath assembly within the vessel will normally induce a significant and prolonged vein spasm. This spasm is desired and beneficial in that it will reduce the inner diameter of the vein being treated, which will cause a corresponding reduction in volume and flow of the blood in the vein. The reduction in blood volume of the target vein limits the extent of dilution of the sclerosant while increasing the amount of drug that will reach the vessel wall. If the targeted vein does not spasm, a vasoconstricting drug such as epinephrine may be injected intravenously through the catheter to induce vessel spasm.

With the distal end hole 19 of the catheter 3 occluded by either the occluding ball 32 or a guidewire 30, the sclerosant is directed through the pressure responsive exits 11 in the catheter wall. This design thus decreases the probability that the sclerosant will migrate to the deep venous system by preventing a forward flowing jet of sclerosant from the distal end hole of the catheter. Advantageously, the sclerosant is prevented from traveling into the central system without the use of an occlusion balloon, manual compression or other adjunct occlusion devices or techniques.

Figure 3C:
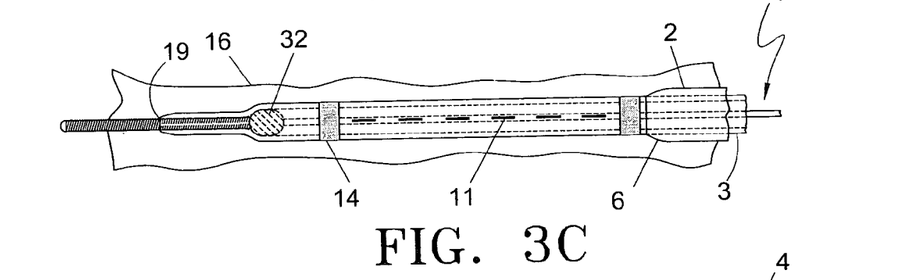
FIG. 3C is a plan view of the vein segment to be treated with sheath partially withdrawn to expose the set of pressure responsive outlets.

Once the catheter/sheath assembly 1 is properly positioned within the targeted vein 16, the sheath 2 is retracted while holding the catheter 3 stationary to expose the desired length of pressure responsive outlet 11 pattern. FIG. 3C illustrates exposure of all outlets 11 in the infusion pattern. The user may adjust the infusion pattern length by withdrawing the sheath 2 to selectively adjust the desired length of the infusion pattern. The sheath 2 will prevent fluid flow through the covered outlets 11 because the fluid follows the path of least resistance and will exit from the non-covered outlets rather than the covered outlets. Radiopaque or ultrasonically visible markers 14 may be provided on the catheter 3 to identify the distal and proximal ends of the maximum infusion outlet zone and on the distal tip 6 section of the sheath 2 to allow the user to discern the location of the sheath 2 relative to the outlet 11 pattern.

Alternatively, the physician may pre-set the exposed infusion zone length prior to inserting the device into the vein. The catheter may optionally contain markings along the shaft to assist in identifying the length of the exposed infusion zone. The sheath hub 5 is aligned with a marking on the catheter that indicates the exposed infusion length. As an example, if a 10 cm infusion zone is desired, the physician aligns the sheath hub to the 10 cm marking on the catheter. A compression gasket may be attached to the sheath hub to ensure that the catheter/sheath alignment remains stationary during insertion and advancement through the target vein.

Sclerosant is delivered under pressure using a standard syringe attached to a Y-hub connector of the catheter 3. Other delivery means may be used such as a pressurized reservoir of sclerosant. As used herein, a sclerosant refers to any fluid that acts upon the inner vessel wall causing a diameter reduction and subsequent vessel wall destruction and occlusion. Sclerosants may include solutions of hypertonic saline, polidocanol, sodium tetradecyl sulfate, chromated gylcerin, iodine and hypertonic glucose. Sclerosant fluid as defined herein may be liquid or foam in varying concentrations. The sclerosant may also be combined with other adjunctive drugs such as vaso-spasming fluid, anesthetics, saline or other fluids. Examples of adjunctive drugs include but are not limited to ephrephrine, Lidocaine and Marcaine. Other sclerosants and adjunctive drugs also fall within the scope of this invention.

The drug may be infused into the catheter 3 in a single bolus or multiple injections of small boluses. It is estimated that a small volume of drug, typically 0.2 cc per bolus, can effectively cover a vein segment of approximately 20 cm in length. Under forceful injections, the fluid advances into the annular fluid passageway 10 formed between the occluding ball wire 4 and the catheter 3 sidewall. Occlusion of the catheter 3 end hole 19 by occluding ball 32 causes the drug to exit from the exposed outlets 11 in the side wall of the catheter 3 into the vein 16.

Figure 3D:
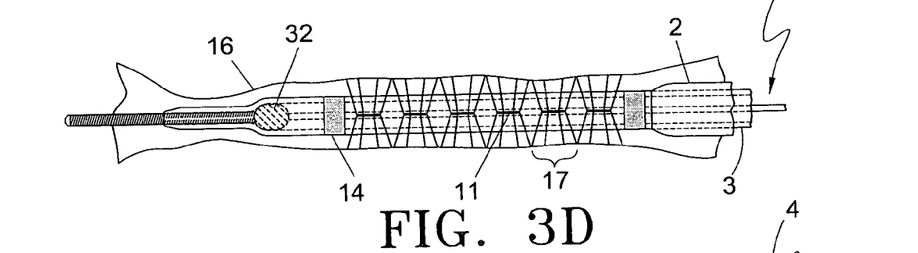
FIG. 3D is a plan view of the vein segment depicting the flow direction of the sclerosant through the catheter lumen and into the wall of the vein.

As described in U.S. Pat. No. 5,250,034, incorporated herein by reference, the outlets 11 are of the same geometry and material and thus the pressure which will open each outlet 11 is the same. When fluid is infused into the catheter lumen 10, the pressure rise within the catheter lumen 10 will be a uniform pressure on all outlets 11. All outlets 11 will open simultaneously at a predetermined internal pressure to allow the drug flow to exit from the catheter lumen 10 in a uniform manner along the entire length of the infusion pattern, as shown in FIG. 3D.

The design and uniform spacing of the pressure responsive outlets 11 ensures uniform and rapid delivery of the sclerosant fluid along the entire vein segment being treated. As illustrated in FIG. 3D, the pressure responsive outlets 11 direct the fluid jet 17 of the drug at a sufficient force to pass through the remaining blood to reach the vein wall without being materially diluted. Once it reaches the vessel wall, the sclerosant will disperse covering a larger area of the vein wall.

Figure 3E:
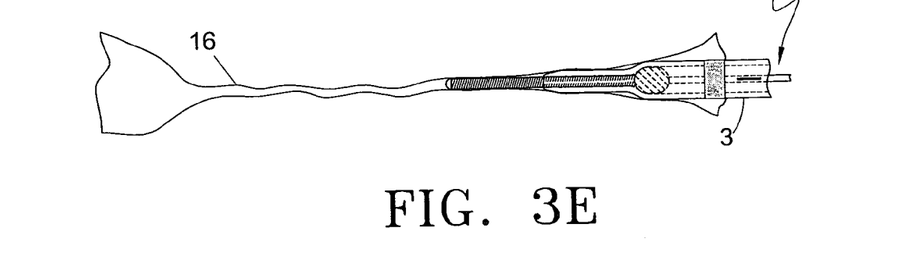
FIG. 3E is a plan view of the vein segment with the catheter/sheath assembly being withdrawn from the treated vein.

The laminar flow of blood through the vein means that the velocity of flow varies from a maximum at the center of the vessel to a zero velocity at the vein wall. Once the sclerosant reaches the vessel wall, the near zero velocity of the blood flow is insufficient to dilute and wash away the drug from the walls. Thus, the design of this invention maximizes the vessel wall/drug contact by directing a high velocity drug column at a high angle (preferably close to 90 degrees) to the vessel wall. The high velocity drug column is directed through the higher velocity blood flow toward the vessel wall where the blood flow is minimal and will not cause dilution of the drug. Applicants believe that the effectiveness of method is enhanced as the column of sclerosant approaches a 90 degree angle relative to the wall of the vessel. In reaction to contact with the sclerosant, the vein wall will further spasm as shown in FIGS. 3D and 3E, whereby further reducing the diameter of the vein.

The physician will deliver single or multiple boluses of drug to the vein to achieve closure, depending on the length of the vein segment being treated. The recommended amount of sclerosant required to achieve permanent closure of the vein is based on inner vein wall surface area. Sufficient sclerosant must be infused to completely cover the vessel wall. Longer vein segments will require more sclerosant.

The method of the current invention is advantageous in that the drug is being delivered directly to the inner vein wall, with minimal or no dilution by the blood. The force of the fluid jet and its directed focus at the vessel wall provide improved drug/wall coverage over prior art methods. The volume of fluid per jet is small but the velocity is high, providing a force capable of penetrating through the blood to contact the vessel wall. Significantly less drug volume is required to achieve the desired impact than volumes required for an end hole catheter or direct injections which are directed into the blood stream where the drug is diluted by the blood flow. The method is also advantageous over sclerotherapy devices that utilize porous material through which the drug is dispersed at lower velocity into the vein, resulting in less sclerosant reaching the vein wall.

If additional sclerosant infusions are desired to ensure complete wall coverage, the injection procedure described above is repeated. Alternatively, the method of this invention may include sequentially delivering sclerosant to segments of the vein. With this method, a shorter catheter or a catheter with a shorter infusion length may be utilized. The sclerosant is first delivered through the catheter to the distal most segment of the vein. After delivering a first bolus of sclerosant, the catheter is repositioned proximally at the next segment to be treated and another injection is delivered to a new section of vein. This process is repeated until the entire length of the vein has been treated. A shorter length catheter device is easier to maneuver and control than a longer length catheter. In addition, a single device can be used to treat various lengths of vein. Thus, this method results in reduction of inventory that must be maintained by the medical facility.

When an effective dose of sclerosant has been delivered to the vein being treated to achieve closure, the catheter/sheath assembly 1 is removed along with the occluding ball wire 4, as illustrated in FIG. 3E. The access site is then closed using method well known the art. The treated leg is then wrapped in compression dressing and covered with a compression stocking to prevent any blood flow through the occluded vein.

Thus, the method disclosed herein provides an effective means of treating varicosities with advantages over prior art treatment methods. The design and operation of the pressure responsive outlets 11 provides an effective means of optimizing vessel wall/drug contact without manual emptying or isolation of the vein segment prior to the procedure. The use of tumescent anesthesia associated with thermal treatments such as RF or endovenous laser closure is eliminated using the method of this invention. Common complications of thermal treatments including vessel perforations, bruising, deep vein thrombosis and skin burns are avoided. The design of the catheter/sheath assembly allows the physician to treat very tortuous vein segments, due to the flexibility and trackability of the catheter. Using a simple catheter/sheath device, a small volume of liquid drug can be optimally administered directly to the vessel wall to achieve effective closure of a vessel. The procedure and method of this invention is easy, uses an inexpensive, uncomplicated device and is fast, safe and effective.

Although the particular embodiments of the method of the present invention have been described in detail, it will be understood that various omissions, modifications, substitutions and changes in the forms and details of the device illustrated and in its operation can be made by those skilled in the art without departing in any way from the spirit of the present invention. Any feature may be combined with another in accordance with the invention and are attended to fall within the scope of the appended claims.

For example, the sheath component may be omitted. Instead, a catheter is inserted over a guidewire and sclerosant is injected through the annular channel as described above. Although the infusion zone length cannot be varied with this embodiment, the elimination of the sheath component provides the user with a less expensive device that is simpler to use. Optionally, catheters with different length infusion zones can be used to accommodate different treatment segment lengths.

As another example, a plurality of small exit holes located in the infusion zone of the catheter shaft may be used to deliver the drug. The exit holes are each of a diameter sufficiently small to provide substantially the same velocity and volume of sclerosant through each exit in a uniform manner along the entire length of the infusion pattern. As an example, circular exits with a diameter of 0.0025" to 0.005" deployed circumferentially and longitudinally along the pre-determined infusion zone will produce a jet of sclerosant at a sufficient force to pass through the remaining blood to reach the vein wall without being materially diluted. The exits may be formed using laser-cutting processes well known in the art.

It is also contemplated that foam sclerosant compositions may provide sufficient flowability characteristics to be usable as a fluid in the method of this invention. Although foams are compressible and will therefore create a lower velocity jet impinging on the vessel wall, foam characteristics including bubble size and air to liquid ratios may be modified to optimize delivery through the device and method described herein whereby achieving the treatment goals of vein wall destruction and subsequent closure. By directing the foam sclerosant through the outlets on the side wall of the catheter at a substantially right angle relative to the vessel wall, smaller volumes of the foam sclerosant may be used with significantly less migration than would occur with an end hole catheter or injection needle. By controlling the migration of foam into the deep venous system, neurological and other treatment complications associated with gas-based sclerosants are minimized. Additionally, directing foam sclerosant through the outlets on the sidewall of the catheter allows the user to specifically target the treatment zone of the vessel.

What is claimed is:

1. The method of treating a vascular disease comprising:
    inserting into a body vessel a catheter having a lumen, an end hole and a plurality of exits longitudinally disposed along the sidewall of said lumen, said end hole having a proximal opening and a distal opening,
    inserting through said catheter an occluding wire having an occluding element having a larger size than the size of said end hole so as to occlude the proximal opening of said end hole, and
    delivering a sclerosant fluid into said lumen under pressure to provide jets of said fluid through said exits that impinge on the wall of the body vessel without using an occlusion balloon and while said end hole is occluded by said occluding element to close the body vessel.

2. The method of claim 1 wherein:
    said exits are disposed circumferentially along said sidewall; and
    said step of delivering includes delivering said fluid along the entire circumference of a predetermined treatment zone of the body vessel.

3. The method of claim 2 wherein said step of delivering includes selecting exits to define an infusion zone which substantially matches a predetermined body vessel treatment zone.

4. The method of claim 2 further comprising the step of: inducing vessel spasm prior to said step of delivering a sclerosant fluid.

5. The method of claim 2 wherein: said step of delivering a sclerosant provides said jets at a substantially uniform velocity.

6. The method of claim 2 wherein said step of inserting into a body vessel a catheter includes inserting a catheter having a plurality of normally closed pressure responsive exits.

7. The method of claim 1 wherein said step of delivering includes delivering jets of said fluid impinging on the wall of the vessel substantially orthogonal to the wall.

8. The method of claim 7 wherein said step of delivering includes selecting exits to define an infusion zone which substantially matches a predetermined body vessel treatment zone.

9. The method of claim 8 wherein said step of inserting into a body vessel a catheter includes inserting a catheter having a plurality of normally closed pressure responsive exits.

10. The method of claim 7 wherein said step of inserting into a body vessel a catheter includes inserting a catheter having a plurality of normally closed pressure responsive exits.

11. The method of claim 1 wherein said step of delivering includes selecting exits to define an infusion zone which substantially matches a predetermined body vessel treatment zone.

12. The method of claim 1 wherein said step of inserting into a body vessel a catheter includes inserting a catheter having a plurality of exits disposed longitudinally along the sidewall of said lumen.

13. The method of claim 1 further comprising the step of: inducing vessel spasm prior to said step of delivering a sclerosant fluid.

14. The method of claim 1 wherein: said step of delivering a sclerosant provides said jets at a substantially uniform velocity.

15. The method of claim 1 wherein: said step of inserting into a body vessel a catheter includes inserting a catheter having a plurality of exits which define an infusion zone encompassed between radiopaque markers.

16. The method of claim 1 wherein said step of inserting through said catheter an occluding wire includes inserting a guide wire having an occluding ball.

17. The method of claim 1 wherein said step of inserting into a body vessel a catheter includes inserting a catheter having a plurality of exits disposed longitudinally and circumferentially along said sidewall.

18. The method of claim 1 wherein said step of inserting into a body vessel a catheter includes inserting a catheter having a plurality of normally closed pressure responsive exits.

19. The method of claim 1 wherein: said step of inserting into a body vessel a catheter includes inserting a sheath over said catheter to substantially block infusion from any exits covered by said sheath.

20. The method of claim 19 wherein: said sheath is positioned after said step of inserting into a body vessel a catheter to uncover a portion of said exits, said portion being the exits through which said step of delivering is effected.

21. The method of claim 19 wherein the step of delivering includes delivering jets of sclerosant fluid along perpendicular lines from said catheter.

22. The method of treating a vascular disease comprising:
inserting into a body vessel a catheter having a lumen, an end hole and a plurality of exits longitudinally disposed along the sidewall of the lumen, said end hole having a proximal opening and a distal opening,
inserting through said catheter an occluding wire having an occluding element having a larger size than the size of said end hole so as to occlude the proximal opening of said end hole,
positioning a sheath over said catheter to uncover all or a portion of said exits, and
delivering a sclerosant fluid into said lumen under pressure to provide jets of said fluid through the uncovered portion of said exits to impinge on the wall of the body vessel substantially orthogonal to the wall vessel without using an occlusion balloon and while said end hole is occluded by said occluding element to close the body vessel.

23. The method of treating a vascular disease comprising:
inserting into a body vessel a catheter having a lumen, an end hole and a plurality of normally closed pressure responsive exits disposed longitudinally and circumferentially along the sidewall of the lumen, said end hole having a proximal opening and a distal opening,
inserting through said catheter an occluding wire having an occluding element having a larger size than the size of said end hole so as to occlude the proximal opening of said end hole,
positioning a sheath over said catheter to uncover all or a portion of said exits, and
delivering a sclerosant fluid into said lumen under pressure to provide jets of said fluid through the uncovered portion of said exits to impinge on the wall of the body vessel substantially orthogonal to the wall vessel without using an occlusion balloon and while said end hole is occluded by said occluding element, the sclerosant fluid being delivered along the entire circumference of a predetermined zone of the body vessel to close the body vessel.

24. The method of claim 23 wherein said step of inserting through said catheter an occluding wire includes inserting an occluding wire having an occluding ball.

25. The method of claim 24 further comprising the step of: inducing vessel spasm prior to said step of delivering a sclerosant fluid.

26. The method of claim 25 wherein: said step of delivering includes the step of opening all of said exposed exits substantially simultaneously at a common pressure.

27. Apparatus for treating a vascular disease comprising:
a body vessel catheter having a lumen, an end hole and a plurality of exits longitudinally disposed along the sidewall of the lumen, said end hole having a proximal opening and a distal opening,
an occluding wire adapted to be inserted through said catheter, said occluding wire having an occluding element having a larger size than the size of said end hole so as to occlude the proximal opening of said end hole,
a delivery device that delivers a sclerosant fluid into said lumen under pressure to pass through said exits as jets which impinge on the wall of the body vessel in which said catheter is deployed without using an occlusion balloon and while said end hole is occluded by said occluding element to close the body vessel.

28. The apparatus of claim 27 wherein said exits are deployed longitudinally and circumferentially along said sidewall.

29. The apparatus of claim 28 wherein said exits are normally closed pressure responsive exits.

30. The apparatus of claim 29 wherein said exits are configured to provide said jets at a substantially uniform velocity.

31. The apparatus of claim 27 wherein said catheter has an end hole opening for a guide wire and said occluding wire includes a guide wire having the occluding element.

32. The apparatus of claim 27 further comprising: a sheath positioned over a portion of said catheter to prevent delivery of said sclerosant from any of said exits covered by said sheath.

33. A method of treating a vascular disease comprising:
inserting into a body vessel a catheter having a lumen, an end hole and a plurality of exits disposed longitudinally along the sidewall of said lumen;
inserting through said catheter an occluding wire that occludes said end hole; and
delivering a sclerosant fluid into said lumen under pressure to provide jets of said fluid through said exits that impinge on the wall of said body vessel without occluding said body vessel and while said endhole is being occluded by said occluding wire to close the body vessel.

* * * * *